United States Patent
Hofsommer et al.

(10) Patent No.: US 12,287,260 B2
(45) Date of Patent: Apr. 29, 2025

(54) PROCESS WATER ANALYSIS SAMPLING ARRANGEMENT

(71) Applicant: HACH LANGE GMBH, Berlin (DE)

(72) Inventors: Daniel Hofsommer, Teltow (DE); Manfred Battefeld, Duesseldorf (DE); Axel Leyer, Moenchengladbach (DE); Sebastian Goertz, Nettetal (DE); Kathrin Otte, Berlin (DE); Frank Steinhauer, Berlin (DE); Hartmut Draeger, Berlin (DE); Aurelia Stellmach-Hanulok, Wuelfrath (DE); Michael Kussmann, Dusseldorf (DE)

(73) Assignee: HACH LANGE GMBH, Berlin (DE)

( * ) Notice: Subject to any disclaimer, the term of this patent is extended or adjusted under 35 U.S.C. 154(b) by 884 days.

(21) Appl. No.: 17/486,942

(22) Filed: Sep. 28, 2021

(65) Prior Publication Data
US 2022/0099537 A1    Mar. 31, 2022

(30) Foreign Application Priority Data

Sep. 30, 2020  (DE) ............... 10 2020 125 547.0

(51) Int. Cl.
| | |
|---|---|
| *G01N 1/14* | (2006.01) |
| *B01D 29/11* | (2006.01) |
| *B01D 61/14* | (2006.01) |
| *B01D 61/18* | (2006.01) |
| *G01N 1/10* | (2006.01) |

(52) U.S. Cl.
CPC .............. *G01N 1/14* (2013.01); *B01D 29/114* (2013.01); *B01D 61/146* (2022.08); *B01D 61/18* (2013.01); *B01D 2315/06* (2013.01); *G01N 2001/1031* (2013.01)

(58) Field of Classification Search
CPC ............ B01D 2315/06; B01D 2321/04; B01D 61/146; B01D 29/114; B01D 2321/18; B01D 65/02; G01N 1/14; G01N 2001/1031; G01N 2001/4088
USPC .......................................... 73/863.23, 864.24
See application file for complete search history.

(56) References Cited

FOREIGN PATENT DOCUMENTS

| CN | 204085988 U | * | 1/2015 | |
|---|---|---|---|---|
| CN | 106932260 A | * | 7/2017 | ............... G01N 1/34 |
| CN | 110124521 A | | 8/2019 | |
| CN | 210613389 U | * | 5/2020 | ............ B01D 35/16 |
| CN | 211784547 U | * | 10/2020 | |

(Continued)

*Primary Examiner* — Daniel S Larkin
*Assistant Examiner* — Nashmiya S Fayyaz
(74) *Attorney, Agent, or Firm* — Ference & Associates LLC

(57) ABSTRACT

A process water analysis sampling assembly includes an immersion probe having a first filter unit and a second filter unit which are fluidically separated from each other, a flushing liquid tank, and a fluidics control. The fluidics control includes a pump arrangement which is fluidically connected to each of the first filter unit and the second filter unit, at least two liquid pumps which are arranged to be mutually independent from each other, and a valve arrangement having plurality of switchable valves. The fluidics control controls a sampling and a flushing of the immersion probe. The fluidic control fluidically connects the flushing liquid tank to one of the first filter unit and the second filter unit and simultaneously connects an analysis unit to the other one of the first filter unit and the second filter unit.

12 Claims, 2 Drawing Sheets

(56) References Cited

FOREIGN PATENT DOCUMENTS

| DE | 198 12 286 A1 | 10/1999 | |
|---|---|---|---|
| DE | 10 2004 037 226 B3 | 8/2005 | |
| EP | 989405 A1 * | 3/2000 | ............... G01N 1/14 |
| JP | 2009533675 A * | 9/2009 | |
| WO | WO-2016055833 A1 * | 4/2016 | ............. G01N 21/05 |

* cited by examiner

PROCESS WATER ANALYSIS SAMPLING ARRANGEMENT

CROSS REFERENCE TO PRIOR APPLICATIONS

Priority is claimed to German Patent Application No. DE 10 2020 125 547.0, filed Sep. 30, 2020. The entire disclosure of said application is incorporated by reference herein.

FIELD

The present invention relates to a process water analysis sampling arrangement comprising an immersion probe and to a fluidics control for controlling sampling and immersion probe cleaning.

BACKGROUND

DE 10 2004 037 226 B3 describes an immersion probe as part of a process water analysis sampling arrangement which comprises a filter unit with two filter membranes which, during continuous and substantially uninterrupted sampling, are continuously cleaned mechanically from the outside by rising gas bubbles emerging from cleaning gas outlets in order to avoid a clogging of the filter membranes. Filter membranes used today can be micro filtration membranes or ultrafiltration membranes which are almost bacteria-proof but which cannot be cleaned sufficiently in the long run via a purely mechanical cleaning of their outer surface. To provide a long service life of an ultrafiltration membrane, backwashing and/or chemical cleaning is required, during which a sampling is unavoidably not possible. A cleaning cycle can last up to one hour, thereby making a continuous or a quasi-continuous sampling impossible.

SUMMARY

An aspect of the present invention is to provide a process water analysis sampling arrangement with a long service life which is suitable for continuous sampling. An aspect of the present invention also to provide a cleaning method for such a sampling arrangement.

In an embodiment, the present invention provides a process water analysis sampling assembly which includes an immersion probe comprising a first filter unit and a second filter unit which are fluidically separated from each other, a flushing liquid tank, and a fluidics control. The fluidics control comprises a pump arrangement which is fluidically connected to each of the first filter unit and the second filter unit, at least two liquid pumps which are arranged to be mutually independent from each other, and a valve arrangement which comprises a plurality of switchable valves. The fluidics control is configured to control a sampling and a flushing of the immersion probe, so that the flushing liquid tank is fluidically connected to one of the first filter unit and the second filter unit, and so that an analysis unit is simultaneously connected to the other one of the first filter unit and the second filter unit.

BRIEF DESCRIPTION OF THE DRAWINGS

The present invention is described in greater detail below on the basis of embodiments and of the drawings in which.

DETAILED DESCRIPTION

Figure 1:
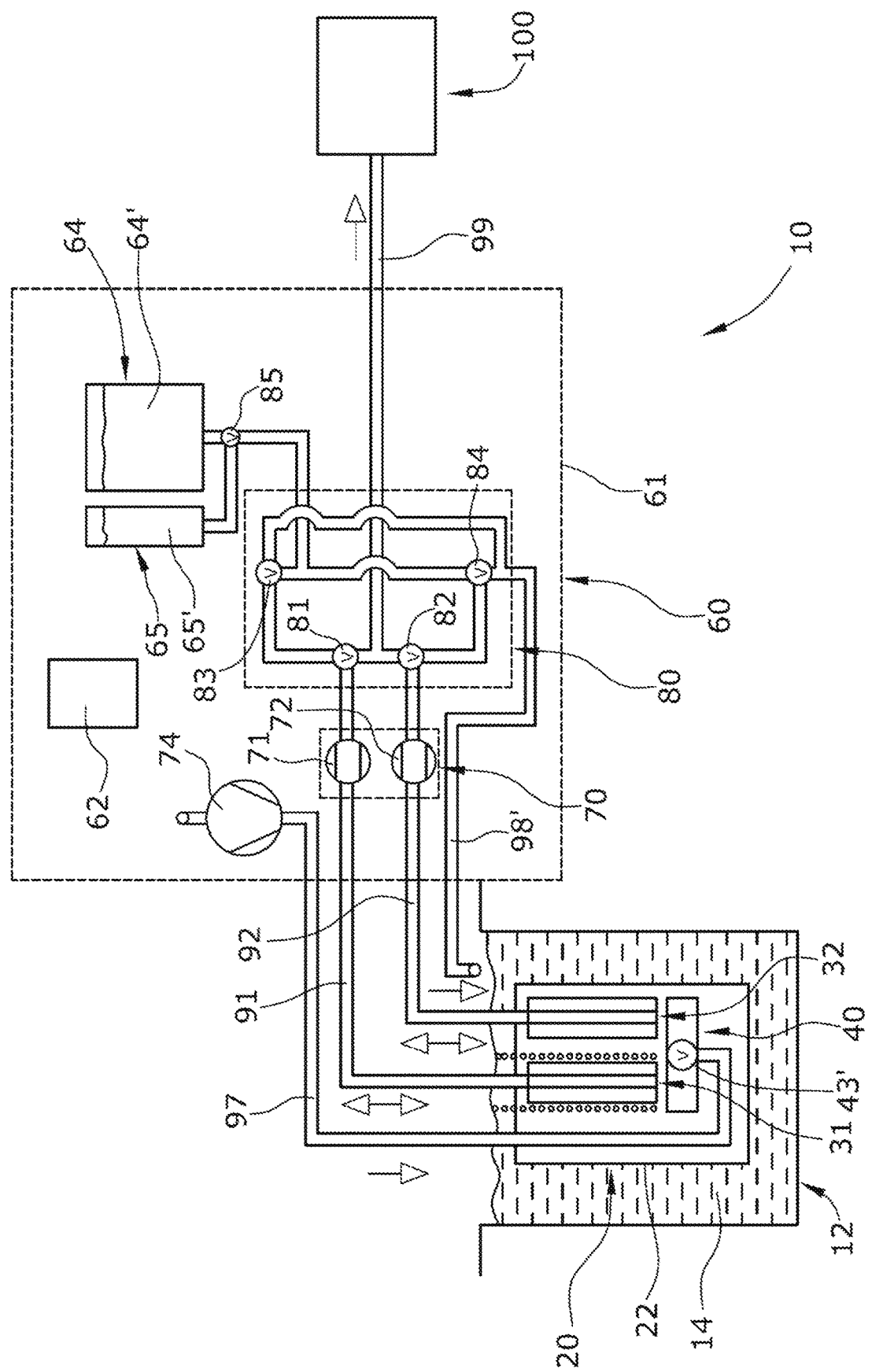
FIG. 1 schematically shows a process water analysis sampling arrangement with an immersion probe immersed in a liquid tank and a shore-side fluidics control.

The process water analysis sampling arrangement according to the present invention comprises an immersion probe, a flushing liquid tank, and a fluidics controller that controls the sampling and the immersion probe flushing. The term "immersion probe" here means a unit which is suitable for being permanently immersed in a liquid, in particular in the wastewater of a wastewater treatment plant.

The flushing liquid tank contains a flushing liquid, for example, water, but which can alternatively be a special flushing liquid. The flushing liquid tank may be located on land, for example, near to or in a structural unit together with the fluidics control. The flushing liquid tank may, however, alternatively comprise a component of the immersion probe and thus be located in the immediate vicinity of the flushing object. The fluidics control consists of both the fluidic components, for example, the pumps and the valves, as well as of the actual control electronics. The fluidics control can, for example, be arranged stationary on land and is therefore, for example, not part of the immersion probe.

The immersion probe comprises at least two fluidically separated filter units, each with a filter membrane, for example, each with a microfiltration or ultrafiltration membrane, which is designed to be bacteria-tight. Fluidic independence of the two filter units from one another means that they can be operated completely separately and independently of one another, for example, one filter membrane in a filter mode and the other filter membrane in a cleaning mode.

The fluidics control comprises a pump arrangement which is fluidically connected to the two filter units and which has at least two mutually independent liquid pumps and a valve arrangement having a plurality of switchable fluidic valves. The fluidics control is designed so that the flushing liquid tank is or can be fluidically connected to one filter unit while, at the same time, the other filter unit is or can be fluidically connected to an analysis unit. The analysis unit contains the analysis device in which a specific chemical component of the liquid sample coming from one filter unit is determined qualitatively or quantitatively. The analysis unit may, for example, comprise as the analysis device a photometer that quantitatively determines, for example, the nitrate content, the phosphate content and/or the ammonium content of the liquid sample.

The fluidics control allows one filter unit to be in the cleaning phase, during which, among other things, the flushing liquid is pumped from the flushing liquid tank to the filter membrane, while at the same time the other filter unit is in the sampling phase, during which a filtered liquid sample is continuously or quasi-continuously pumped from the respective filter unit to the analysis unit. The term "flushing liquids" are here understood to be both purely flushing liquids and additionally actively cleaning liquids. The flushing phases and the sampling phases can alternately be controlled so that the sampling arrangement can provide a liquid sample quasi-continuously for the analysis unit. A high-frequency cleaning of the filter membranes can thereby be carried out without significantly interrupting the sampling process even when bacteria-proof ultrafiltration membranes are used.

The immersion probe can, for example, comprise a cleaning gas outlet which is arranged at the vertically lower end of each filter unit, which can be selectively supplied with a cleaning gas, for example, ambient air, via a cleaning gas pump. The cleaning gas exiting the cleaning gas outlet generates a cleaning gas carpet of cleaning gas bubbles distally, i.e., on the outside of the respective filter unit, via which the distal liquid boundary layer of the filter membrane is turbulently engulfed. Excessive clogging of the filter membrane with solid particles can thereby be substantially inhibited during the sampling phase. The cleaning gas carpet can be used to carry away the flushing liquid at the end of the cleaning phase. The combination of cleaning the filter membranes with a flushing liquid and the application of a cleaning gas carpet at the outside of the respective filter membrane considerably extends the service life, i.e., the maintenance interval, of the filter units until the filter membranes requires replacement.

The sampling arrangement can, for example, comprise a waste line which is fed by the fluidics control during a backwashing of the filter unit with a backwashing liquid of the respective filter unit, the waste line, for example, terminating inside the immersion probe. The flushing liquid is introduced, for example, into a wet area of the immersion probe which is spatially arranged between the backs of the two filter units. The wet area is laterally open so that the flowing wastewater constantly flows therethrough and the flushing liquid cannot be sucked in as part of the liquid sample taken by the immersion probe.

The two liquid pumps of the fluidics control can, for example, be designed to be bidirectional, i.e., they can each be operated in both pumping directions. Due to the bidirectional operability of the two liquid pumps, the total number of liquid pumps can, for example, be reduced to two liquid pumps. The two liquid pumps can, for example, each be designed as peristaltic hose pumps. Peristaltic hose pumps are reliable, easily reversible in their pumping direction without requiring additional valves, and the fluidic part of the hose pump can be easily replaced, for example, during maintenance. The relatively large volumetric inaccuracy inherent in a peristaltic pump is thereby not relevant in sample taking.

The fluidics control or the immersion probe can, for example, comprise a cleaning gas switching valve through which the cleaning gas can be directed either to one cleaning gas outlet or to the other cleaning gas outlet. The cleaning gas coming from the cleaning gas pump is thus already branched in the fluidics control or alternatively just within the immersion probe, and is optionally directed to one, to the other, or to both filter units simultaneously.

The two liquid pumps can, for example, be fluidically arranged so that they are each assigned to a single particular filter unit. Each liquid pump thus either pumps a liquid sample from its associated filter unit to the analysis unit or pumps the flushing liquid to the same filter unit. The liquid pumps are thus associated with a filter unit, but are not associated with a single specific pumping task. Since each liquid pump is flowed through by a flushing liquid, each of the liquid pumps is thereby periodically flushed during the flushing phase of the associated filter unit. A separate flushing of the respective liquid pump is therefore not necessary.

In an embodiment of the present invention, two liquid tanks can, for example, be provided for two different flushing liquids, one liquid tank containing a basic flushing liquid and the other liquid tank containing an acidic flushing liquid. The filter units or filter membranes are thus cleaned by two different stored flushing liquids, which are applied one after the other. This fundamentally increases cleaning quality.

Although cleaning a filter unit with two different cleaning liquids generally takes longer than cleaning with a single flushing liquid, this is here not relevant since, during the cleaning phase of one filter unit, the other filter unit is continuously available for sampling.

The fluidics control can, for example, be located on land and outside the immersion probe. The term "on land" as used herein is understood to mean that the fluidics control is fixed on land, i.e., is not immersed in the liquid within the tank.

The present invention also provides a process for operating the process water analysis sampling arrangement which includes the following method steps:

Switching the valve arrangement so that the flushing liquid is pumped from the flushing liquid tank through the one liquid pump to the one filter unit and; simultaneously, Pumping a liquid sample through the other liquid pump from the other filter unit to a sample outlet of the fluidics control. The liquid sample thereby flows to the analysis unit from the fluidics control sample outlet.

The flushing of the filter unit with the flushing liquid can, for example, be followed by the process step of switching the valve arrangement and switching the pumping direction of the one liquid pump so that a backflushing of the one filter unit takes place. The term "backflushing" is here understood to be that the liquid pump, which is in the flushing phase, is operated in a suction mode so that liquid is sucked in from a distal side through the filter membrane. This liquid is pumped by the liquid pump through a waste line to a waste end. The respective filter membrane is thereby flushed free of the flushing liquid.

The process step following the flushing of the filter unit can, for example, provide that the cleaning gas pump is switched on and the cleaning gas outlet of the filter unit in question is fluidically controlled so that the one filter unit, which is in the flushing phase, is distally covered with a cleaning gas carpet. During the flushing of the one filter unit with the flushing liquid, no cleaning gas carpet is applied in order to provide that the flushing liquid remains in the distal boundary layer of the filter membrane and that the chemical effect of the flushing liquid is not weakened.

Two embodiments of the present invention are explained in greater detail below under reference to the drawings.

Figure 2:
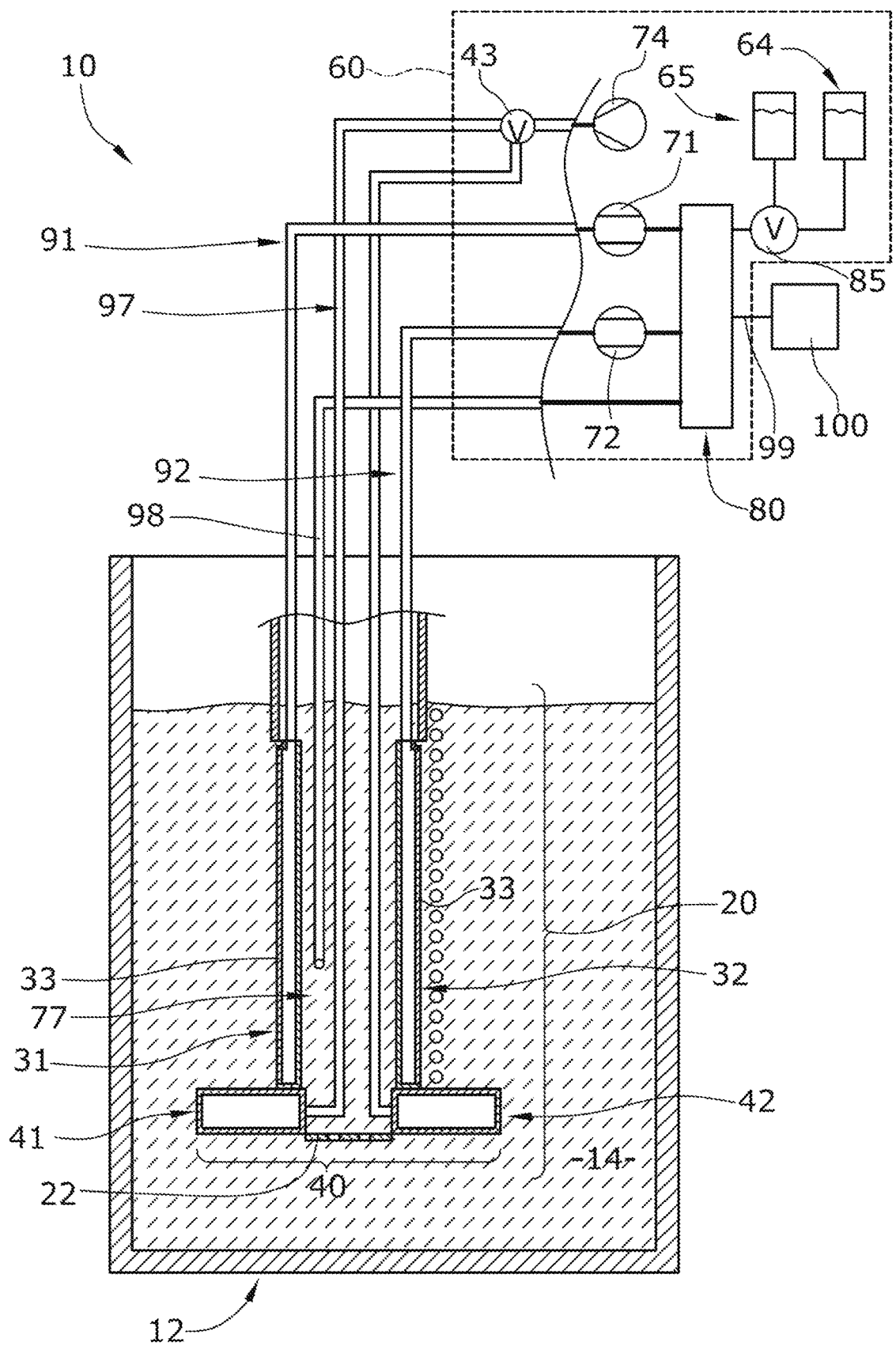
FIG. 2 shows a second version of the sampling arrangement with a schematic horizontal section of the immersion probe.

FIG. 1 schematically illustrates a process water analysis sampling arrangement 10 with an immersion probe 20, a separate landside fluidics control 60, and a landside analysis unit 100. The immersion probe 20 is completely immersed in the wastewater 14 of a wastewater treatment tank 12, as is shown in FIG. 2. The landside fluidics control 60 controls the sampling and flushing of the immersion probe 20.

As shown in particular in FIG. 2, the immersion probe 20 comprises within a stainless-steel immersion probe frame 22 two fluidically separated filter units 31,32, each of which have at least one filter membrane 33. The filter membrane 33 has its distal side in direct contact with the wastewater 14. The proximal side of the filter membrane 33 is fluidically connected via a filter line 91,92 with a respective liquid pump 71,72, which is part of the landside fluidics control 60. The two liquid pumps 71,72 are each designed as a bidirectional peristaltic hose pump and together define a pump arrangement 70.

The rectangular filter membrane 33 is in the present case a so-called ultrafiltration membrane which has very small pores, for example, with an exclusion limit of 500-5 um, is designed to be bacteria-proof, and which is therefore generally relatively sensitive to clogging or overgrowth.

A respective cleaning gas outlet 41,42 is arranged at the vertical lower end of each filter unit 31,32 which can be selectively supplied with a cleaning gas, in this case ambient air, by a cleaning gas pump 74 which is part of the landside fluidics control 60. Each respective cleaning gas outlet 41,42 is a substantially fluidically closed hollow body which comprises on its upper side a plurality of small openings through which the cleaning gas can exit and rise in the form of gas bubbles. The gas bubbles cover the entire distal side or surface of the respective filter membrane 33 in a carpet-like manner, as shown on the second (right) filter unit 32 in FIG. 2.

A 3-way cleaning gas valve 43' is provided within the immersion probe 20 of FIG. 1 through which the cleaning gas coming through a cleaning gas line 97 can be fluidically directed to one or both cleaning gas outlets 41,42 so that a cleaning gas carpet composed of gas bubbles rises on the distal surface of the respective filter membrane 33. The two cleaning gas outlets 41,42 and the cleaning gas valve 43 together define a mechanical gas cleaning arrangement 40. In the second embodiment of FIG. 2, the cleaning gas valve 43 is arranged within the landside fluidics control 60 so that no electrical components are installed in the immersion probe 20.

The landside fluidics control 60, which is housed in a fluidics control housing 61, comprises a valve arrangement 80 which comprises four electromagnetically switchable 3-way valves 81, 82, 83, 84, two flushing liquid tanks 64, 65, a flushing liquid switching valve 85, and an electronic control device 62. One flushing liquid tank 64 contains a basic flushing liquid 64' and the other flushing liquid tank 65 contains an acidic flushing liquid 65'.

The four valves 81-84 of the valve arrangement 80 can each be switched by the electronic control device 62 to selectively fluidically connect each of the two filter units 31,32 to the sample outlet 99, the waste line 98, or to one of the two flushing liquid tanks 64,65.

The landside fluidics control 60 is fluidically connected directly to the two independent liquid pumps 71,72 via two pump ports, to a waste line 98 via a waste line 98', to the two flushing liquid tanks 64,65 via a flushing liquid port, and to a sample outlet 99 of the landside fluidics control 60 via a sample port. A sample line leads from the sample outlet 99 to the landside analysis unit 100, which comprises a photometer as the analyzer.

As shown in FIG. 1, the waste line 98' leads and discharges with a short path into the wastewater treatment tank 12. As shown in FIG. 2, the waste line 98 may alternatively terminate in a wet area 77 within the immersion probe 20.

The pump arrangement 70 and valve arrangement 80 allow only two liquid pumps 71,72 to control all of the liquid fluidics of the sampling arrangement 10.

In the arrangement shown in FIG. 1, the two liquid pumps 71,72 and the valve arrangement 80 are configured or controlled so that a liquid sample from the wastewater 14 is pumped from the first (left) filter unit 31 through the one liquid pump 71 to the sample outlet 99, while at the same time the second (right) filter unit 32 is fed first with the basic flushing liquid 64' from the one flushing liquid tank 64 and then with the acidic flushing liquid 65' from the other flushing liquid tank 65. The cleaning gas valve 43, 43' is switched so that only the first (left) filter unit 31, which is in sampling mode, is supplied with the cleaning gas. At the end of the cleaning of the second (right) filter unit 32, the pumping direction of the associated liquid pump 72 and the valve arrangement 80 are switched so that backflushing of the second (right) filter unit 32 with wastewater 14 is carried out, which is fed into the waste line 98. Simultaneously, during the backflushing, a cleaning gas carpet is also applied to the second (right) filter unit 32. After finishing the cleaning cycle of the second (right) filter unit 32, the pump arrangement 70 and the valve arrangement 80 are controlled and switched over so that the second (right) filter unit 32 is used for sampling and is fluidically connected to the sample outlet 99, whereas the first (left) filter unit 31 is cleaned with the cleaning cycle previously described.

The landside analysis unit 100 is thereby supplied with a liquid sample of the wastewater 14 substantially continuously and substantially without interruption.

The present invention is not limited to embodiments described herein; reference should be had to the appended claims.

LIST OF REFERENCE NUMERALS

10 Process water analysis sampling arrangement
12 Wastewater treatment tank
14 Wastewater
20 Immersion probe
22 Immersion probe frame
31 First (left) filter unit
32 Second (right) filter unit
33 Filter membrane
40 Mechanical gas cleaning arrangement
41 Cleaning gas outlet
42 Cleaning gas outlet
43 Cleaning gas valve
43' 3-way cleaning gas valve
60 Landside fluidics control
61 Fluidics control housing
62 Electronic control device
64 Flushing liquid tank
64' Basic flushing liquid
65 Flushing liquid tank
65' Acidic flushing liquid
70 Pump arrangement
71 Liquid pump
72 Liquid pump
74 Cleaning gas pump
77 Wet area
80 Valve arrangement
81 3-way valve
82 3-way valve
83 3-way valve
84 3-way valve
85 Flushing liquid switching valve
91 Filter line
92 Filter line
97 Cleaning gas line
98 Waste line
98' Waste line
99 Sample outlet
100 Landside analysis unit

What is claimed is:

1. A process water analysis sampling assembly comprising:
   an immersion probe comprising a first filter unit and a second filter unit which are fluidically separated from each other;
   a flushing liquid tank; and
   a fluidics control comprising,
      a pump arrangement comprising at least two liquid pumps which is fluidically connected to each of the first filter unit and the second filter unit, each of the first filter unit and second filter unit fluidically connected to a single pump of the at least two liquid pumps, the at least two liquid pumps comprising a first liquid pump and a second liquid pump which are arranged to be mutually independent from each other, and a valve arrangement which comprises a plurality of switchable valves, the fluidics control being configured, to control a sampling and a flushing of the immersion probe filter units, so that the flushing liquid tank is fluidically connected to one of the first filter unit and the second filter unit, and switching the valve arrangement to an arrangement to allow fluidic connection from the flushing liquid tank through the first liquid pump to the first filter unit and simultaneously collecting a liquid sample through the second liquid pump from the second filter unit to a sample outlet, alternatively the valve arrangement can be switched to allow fluidic connection from the flushing liquid tank through the second liquid pump to the second filter unit and simultaneously collecting a liquid sample through the first liquid pump from the first filter unit to the sample outlet, and an analysis unit is simultaneously connected to the sample outlet to collect the liquid sample.

2. The process water analysis sampling arrangement as recited in claim 1, further comprising:

a cleaning gas pump which is configured to pump a cleaning gas, wherein the immersion probe further comprises, a first cleaning gas outlet which is arranged at a vertically lower end of the first filter unit, and a second cleaning gas outlet which is arranged at a vertically lower end of the second filter unit, wherein, each of the first cleaning gas outlet and the second cleaning gas outlet are configured to be selectively supplied with the cleaning gas via the cleaning gas pump.

3. The process water analysis sampling arrangement as recited in claim 2, wherein the fluidics control or the immersion probe further comprises a cleaning gas switching valve through which the cleaning gas can be selectively directed to the first cleaning gas outlet or to the second cleaning gas outlet.

4. The process water analysis sampling arrangement as recited in claim 1, further comprising:

a waste line which is arranged to terminate in the immersion probe, wherein, the fluidics control is further configured to feed the waste line during a backwashing of the first filter unit or of the second filter unit with a backwashing liquid of the respective first filter unit or the second filter unit.

5. The process water analysis sampling arrangement as recited in claim 1, wherein the at least two liquid pumps are provided to be bidirectional.

6. The process water analysis sampling arrangement as recited in claim 5, wherein the at least two liquid pumps are peristaltic hose pumps.

7. The process water analysis sampling arrangement as recited in claim 1, wherein each one of the at least two liquid pumps is permanently fluidically associated with one of the first filter unit or the second filter unit.

8. The process water analysis sampling arrangement as recited in claim 1, further comprising an another liquid flushing tank:

wherein, one of the flushing liquid tank and the another flushing liquid tank contains a basic flushing liquid, and the other one of the flushing liquid tank and the another flushing liquid tank contains an acidic flushing liquid.

9. The process water analysis sampling arrangement as recited in claim 1, wherein the fluidics control is arranged on land and externally of the immersion probe.

10. A method of operating the process water analysis sampling arrangement as recited in claim 1, the method comprising:

providing the process water analysis sampling arrangement as recited in claim 1, wherein, the flushing liquid tank is configured to pump a flushing liquid;

switching the valve arrangement so that the flushing liquid is pumped from the flushing liquid tank through one of the at least two liquid pumps to one of the first filter unit and the second filter unit, and, simultaneously therewith, pumping a liquid sample through the otherone of the at least two liquid pumps from the other one of the first filter unit and the second filter unit to the sample outlet of the fluidics control.

11. The method as recited in claim 10, wherein, after the switching of the valve arrangement, the method further comprises:

switching the valve arrangement and the pumping direction of the one of the two liquid pumps so that the one of the first filter unit and the second filter unit is backwashed.

12. The method as recited in claim 10, wherein, the process water analysis sampling arrangement as recited in claim 1 further comprises a cleaning gas pump which is configured to pump a cleaning gas, the immersion probe of the process water analysis sampling arrangement as recited in claim 1 further comprises, a first cleaning gas outlet which is arranged at a vertically lower end of the first filter unit, and a second cleaning gas outlet which is arranged at a vertically lower end of the second filter unit, wherein, each of the first cleaning gas outlet and the second cleaning gas outlet are configured to be selectively supplied with the cleaning gas via the cleaning gas pump, and after the switching of the valve arrangement, the method further comprises:

switching on the cleaning gas pump; and switching one of the first cleaning gas outlet and the second cleaning gas outlet so that the one of the first filter unit and the second filter unit is covered distally with a cleaning gas carpet.

* * * * *